(12) United States Patent
McConnell et al.

(10) Patent No.: US 10,881,674 B2
(45) Date of Patent: *Jan. 5, 2021

(54) SYNTHETIC COMPOSITION FOR TREATING METABOLIC DISORDERS

(71) Applicant: GLYCOM A/S, Høsholm (DK)

(72) Inventors: Bruce McConnell, La Tour de Peilz (CH); Louise Kristine Vigsnæs, København (DK); Emma Elison, Hjärup (SE)

(73) Assignee: GLYCOM A/S, Horsholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/183,404

(22) Filed: Jun. 15, 2016

(65) Prior Publication Data

US 2016/0367577 A1    Dec. 22, 2016

Related U.S. Application Data

(63) Continuation-in-part of application No. 15/104,794, filed as application No. PCT/DK2015/050385 on Dec. 8, 2015.

(30) Foreign Application Priority Data

Dec. 8, 2014  (DK) .................................. 2014 70768

(51) Int. Cl.
*A61K 31/702* (2006.01)
*A61K 9/00* (2006.01)
*A61K 9/20* (2006.01)

(52) U.S. Cl.
CPC .......... *A61K 31/702* (2013.01); *A61K 9/0053* (2013.01); *A61K 9/0095* (2013.01); *A61K 9/2054* (2013.01)

(58) Field of Classification Search
CPC ............................ A61K 31/702; A61K 9/0053
USPC ......................................................... 514/61
See application file for complete search history.

(56) References Cited

U.S. PATENT DOCUMENTS

| | | | |
|---|---|---|---|
| 4,895,838 A | 1/1990 | McCluer et al. | |
| 5,906,982 A | 5/1999 | Prieto et al. | |
| 2011/0189149 A1 | 8/2011 | Burcelin et al. | |
| 2011/0256233 A1* | 10/2011 | Fournell | A23C 9/1422 424/535 |
| 2012/0171165 A1* | 7/2012 | Buck | A61K 31/702 514/23 |
| 2012/0208782 A1 | 8/2012 | Frantz | |
| 2012/0294840 A1* | 11/2012 | Newburg | C07H 3/06 424/93.44 |
| 2014/0037785 A1 | 2/2014 | Barboza et al. | |
| 2015/0010670 A1 | 1/2015 | Mills et al. | |

FOREIGN PATENT DOCUMENTS

| | | |
|---|---|---|
| EP | 0691079 A2 * | 10/1996 |
| EP | 1332759 | 8/2003 |
| EP | 2143341 | 1/2010 |
| EP | 2332552 | 6/2011 |
| WO | 98/43495 A1 | 10/1998 |
| WO | WO0104341 | 1/2001 |
| WO | 2007/073192 A2 | 6/2007 |
| WO | WO2007101862 | 9/2007 |
| WO | WO2009000803 | 12/2008 |
| WO | 2009/077352 A1 | 6/2009 |
| WO | 2009/082214 A1 | 7/2009 |
| WO | WO2010115934 | 10/2010 |
| WO | WO2010115935 | 10/2010 |
| WO | WO2011100979 | 8/2011 |
| WO | WO2011100980 | 8/2011 |
| WO | 2011/119023 A1 | 9/2011 |
| WO | WO2011119033 | 9/2011 |
| WO | WO2012007588 | 1/2012 |
| WO | WO2012076323 | 6/2012 |
| WO | WO2012092153 | 7/2012 |
| WO | WO2012107865 | 8/2012 |
| WO | WO2012113404 | 8/2012 |
| WO | WO2012113405 | 8/2012 |
| WO | WO2012127410 | 9/2012 |
| WO | WO2012155916 | 11/2012 |
| WO | WO2012156897 | 11/2012 |
| WO | WO2012156898 | 11/2012 |
| WO | WO2012158517 | 11/2012 |
| WO | WO2013036104 | 3/2013 |
| WO | 2013/057061 A1 | 4/2013 |
| WO | WO2013044928 | 4/2013 |
| WO | WO2013057061 | 4/2013 |
| WO | WO2013091660 | 6/2013 |
| WO | WO2013139344 | 9/2013 |
| WO | WO2013154725 | 10/2013 |
| WO | 2014/043330 A1 | 3/2014 |

(Continued)

OTHER PUBLICATIONS

Anatolltou (Journal of Pediatric and Neonatal Individualized Medicine 2012;1(1):11-18).*
Asakuma et al. (European journal of clinical nutrition, (Apr. 2008) vol. 62, No. 4, pp. 488-494).*
Kresser (https://chriskresser.com/a-healthy-gut-is-the-hidden-key-to-weight-loss; Oct. 29, 2010).*
Cani et al. (Diabetes, vol. 56, Jul. 2007, 1761-1772).*
Burcelin, R. et al, "The gut microbiota ecology: a new opportunity for the treatment of metabolic diseases?", Frontiers in Bioscience, vol. 14, pp. 5107-5117, (Jun. 2009).
Backhed, F. et al, "The gut microbiota as an environmental factor that regulates fat storage", PNAS, 101:44:15718-15723, (Nov. 2, 2004).
Qin, J. et al, "A metagenome-wide association study of gut microbiota in type 2 diabetes", Nature, vol. 490, 55-60, (Oct. 2012).

(Continued)

Primary Examiner — Eric Olson
Assistant Examiner — Michael C Henry
(74) Attorney, Agent, or Firm — Kunzler Bean & Adamson

(57) ABSTRACT

The invention relates to a method for stabilising or reducing insulin resistance in patients having an obesity-related, metabolic disorder, the method comprising administering to the patient an effective amount of one or more human milk oligosaccharides (HMOs).

12 Claims, No Drawings

Specification includes a Sequence Listing.

(56) References Cited

FOREIGN PATENT DOCUMENTS

| | | |
|---|---|---|
| WO | WO2014164882 | 10/2014 |
| WO | 2014/187464 A1 | 11/2014 |
| WO | WO2014187464 | 11/2014 |
| WO | WO2015071401 | 5/2015 |
| WO | WO2015071402 | 5/2015 |
| WO | WO2015071403 | 5/2015 |
| WO | 2015/164021 A1 | 10/2015 |
| WO | 2016/091265 A1 | 6/2016 |
| WO | 2017/129639 A1 | 8/2017 |
| WO | 2017/129641 A1 | 8/2017 |
| WO | 2017/129648 A1 | 8/2017 |
| WO | 2017/129650 A1 | 8/2017 |

OTHER PUBLICATIONS

Ley, R. et al, "Microbial ecology: human gut microbes associated with obesity", Nature, vol. 4-44, pp. 1022-1023, (Dec. 2006).

Tremaroli, V. et al, "Functional interactions between the gut microbiota and host metabolism", Nature, 489:7415:242-249, (Sep. 2012)).

Cani, P. et al, "Changes in gut microbiota control inflammation in obese mice through a mechanism involving GLP-2-driven improvement of gut permeability", Gut, vol. 58, pp. 1091-1103, (2009).

Kootte, R. et al, "The therapeutic potential of manipulating gut microbiota in obesity and type 2 diabetes mellitus", Diabetes, Obesity & Metabolism, vol. 14, pp. 112-120, (2012).

Turnbaugh, P. et al, "An obesity-associated gut microbiome with increased capacity for energy harvest", Nature, vol. 444, pp. 1027-1031, (Dec. 2006)).

Rani, P. et al, "Changes in gut microbiota control metabolic endotoxemia-induced inflammation in high-fat diet-induced obesity and diabetes in mice", Diabetes, vol. 57, pp. 1470-1481, (Jun. 2008).

Cani, P, et al, "Involvement of endogenous glucagon-like peptide-1(7-36) amide on glycaemia-lowering effect of oligofructose in streptozotocin-treated rats", J. of Endocrinology, vol. 185, pp. 457-465, (2005).

Cani, P. et al, "Metabolic endotoxemia initiates obesity and insulin resistance", Diabetes, vol. 56, pp. 1761-1772, (Jul. 2007).

Fearnley, G. et al, "Reduction of blood fibrinolytic activity in diabetes mellitus by insulin", The Lancet, 2(7111):1067, doi:10.1016/S0140-6736(59)91534-X, (Dec. 1959).

Ogston, D. et al, "Fibrinolysis in obesity", The Lancet, 284(7371):1205-1207, (Dec. 5, 1964).

Hotamisligil, G. et al, "IRS-1-mediated inhibition of insulin receptor tyrosine kinase activity in a TNF-alpha-and obesity-induced insulin resistance", Science, 271(5249):665-670, (Feb. 2, 1996).

Uysal, K. et al, "Protection from obesity-induced insulin resistance in mice lacking TNF-alpha function", Nature, vol. 389, pp. 610-614, (Oct. 9, 1997).

Amar, J. et al, "Intestinal mucosal adherence and translocation of commensal bacteria at the early onset of type 2 diabetes: molecular mechanisms and probiotic treatment", EMBO Molecular Medicine, vol. 3, pp. 559-572, (2011).

Andersson, A. et al, "Comparative analysis of human gut microbiota by barcoded pyrosequencing", PlosOne, 3(7): e2836, (Jul. 2008).

IDF Diabetes Atlas, International Diabetes Federation, 6th edition.

Urashima, T. et al, "Milk oligosaccharides", Nova Biomedical Books, NY, (2011).

Bezirtzoglou, E. et al, "Microbiota profile in feces of breast-and-formula-fed newborns by using fluorescence in situ hybridization", Anaerobe, vol. 17, pp. 478-482, (2011).

Bottacini, F. et al, "Diversity, ecology and intestinal function of bifidobacteria", Microbial Cell Factories, vol. 13, Suppl. 1, pp. S4, (2014).

Boulange, C. et al, "Impact of the gut microbiota on inflammation, obesity, and metabolic disease", Genome Medicine, 8:42, (2016).

Bridger, T., "Childhood obesity and cardiovascular disease", Paediatr. Child Health, 14(3):177-182, (2009).

Bruggencate, S. et al, "Functional role and mechanisms of sialyllactose and other sialyated milk pligosaccharides", Nutrition Reviews, 72(6):377-389, (2014).

Cani, P. et al, "Gut microbiota fermentation of prebiotics increases satietogenic and incretin gut peptide production with consequences for appetite sensation and glucose response after a meal", American J. of Clinical Nutrition, vol. 30, pp. 1236-1243, (2009).

Cano, P. et al, "Bifidobacterium CECT 7765 improves metabolic and immunological alterations associated with obesity in high-fat diet-fed mice", Obesity, 21(11):2310-2321, (Nov. 2013).

Chakraborti, C., "New-found link between microbiota and obesity", World J. of Gastrointestinal Pathophysiology, 6(4):110-119, (Nov. 2015).

Chichlowski, M. et al, "Bifidobacteria isolated from infants and cultured on human milk oligosaccharides affect intestinal epithelial function", J. Pediatr. Gastroenterol Nutrition, 55(3):321-327, (Sep. 2012).

Conterno, L. et al, "Obesity and the gut microbiota: does up-regulating colonic fermentation protect against obesity and metabolic disease?", Genes Nutrition, 6:241-260, (2011).

Nuckols, C., "The diagnostic and statistical manual of mental disorders, fifth edition (DSM-5)", American Psychiatric Association, 5th edition, (2013).

Dinan, T. et al, "Psychobiotics: A novel class of psychotropic", Biol. Psychiatry, 74:720-726, (2013).

Ferrari, A. et al, "Burden of depressive disorders by country, sex, age, and year: Findings from the global burden of disease study 2010", PLOS Medicine, 10(11):e1001547, (Nov. 2013).

Fukuda, S. et al, "Bifidobacteria can protect from enteropathogenic infection through production of acetate", Nature, vol. 469, pp. 543-549, (Jan. 2011).

Gabrielli, O. et al, "Preterm milk oligosaccharides during the first month of lactation", Pediatrics, vol. 128, pp. e1520-e1531, (Nov. 2011).

Gill, S. et al, "Metagenomic analysis of the human distal gut microbiome", Science, 312(5778):1355-1359, (Jun. 2006).

Jokela, M. et al, "Association of metabolically healthy obesity with depressive symptoms: pooled analysis of eight studies", Molecular Psychiatry, vol. 19, pp. 1-5, (2013).

Kendler, K. et al, "Illicit psychoactive substance use, abuse and dependence in a population-based sample of Norwegian twins", Psychol. Med., 36(7):955-962, (Jul. 2006).

Matthan, N. et al, "Sex-specific differences in predictive value of cholesterol homeostasis markers and 10-year cardiovascular disease event rate in Framingham offspring study participants", J. American Heart Assn., vol. 2, pp. e005066-e005079,(2013).

Rolland-Cachera, M., "Childhood obesity: current definitions and recommendations for their use", Intl. J. of Pediatric Obesity, vol. 6, pp. 325-331, (2011).

Sanchez, M. et al, "Childhood obesity: A role for gut microbiota?", Intl. J. of Environ. Res. Public Health, vol. 12, pp. 162-175, (2015).

Savignac, H. et al, "Bifidobacteria exert strain-specific effects on stress-related behavior and physiology in BALB/c mice", Neurogastroenterology & Motility, vol. 26, pp. 1615-1627, (2014).

Schwiertz, A. et al, "Microbiota and SCFA in lean and overweight healthy subjects", Obesity, 18(1):190-195, (Jan. 2010).

Shah, M. et al, "Effects of GLP-1 on appetite and weight", Rev. Endocr. Metab. Disorder, 15(3):181-187, (Sep. 2014).

Tarr, A. et al, "The prebiotics 3'sialyllactose and 6'sialyllactose diminish stressor-induced anxiety-like behavior and colonic microbiota alterations: evidence for effects on the gut-brain axis", Brain Behav. Immun., vol. 15, pp. 181-215, (2015).

Verbeke, K. et al, "Towards microbial fermentation metabolites as markers for health benefits of prebiotics", Nutrition Research Reviews, vol. 28, pp. 42-66, (2015).

Walter, J. et al, "Detection and identification of gastrointestinal *Lactobacillus* species by using denaturing gradient gel electrophoresis and species-specific PCR primers", Appl. Environ. Microbiol., 66(1):297-303, (Jan. 2000).

Anonymous, "Obesity and overweight", WHO, Media Centre fact sheet, pp. 1-5, (Jan. 2015).

(56) References Cited

OTHER PUBLICATIONS

Zhang, C. et al, "Dietary modulation of gut microbiota contributes to alleviation of both genetic and simple obesity in children", EbioMedicine, vol. 2, pp. 966-982, (2015).
Qin, J. et al, "A human gut microbial gene catalogue established by metagenomic sequencing", Nature, vol. 464, pp. 39-65, (2010).
Ettinger, G. et al, "The influence of the human microbiome and probiotics on cardiovascular health", Gut Microbes, 5:6:719-728, (2014).
Duranti, S. et al, "Exploration of the genomic diversity and core genome of the bifidobacterium adolescentis phylogenetic group by means of a polyphasic approach", Applied and Environmental Microbiology, 79(1):336-346, (Jan. 2013).
U.S. Appl. No. 15/183,391, Final Office Action Summary, dated Sep. 11, 2017.
PCT/DK2017/050198, "Notification of Transmittal of the International Search Report and the Written Opinion of the International Searching Authority, or the Declaration", Aug. 23, 2017, 20 pages.
U.S. Appl. No. 15/183,391, Office Action Summary, dated Feb. 24, 2017.
U.S. Appl. No. 15/183,431, Office Action Summary, dated Oct. 13, 2017.
Anatolltou, "Human Milk Benefits and Breastfeeding", Journal of Pediatric and Neonatoal Individualized Medicine, 2012; 1(1), pp. 11-18.
Asanuma et al., "Variation of Major Neutral Oligosaccharides Levels in Human Colostrum", European Journal of clinical Nutrition, Apr. 2008, vol. 62, No. 4, pp. 488-494.
U.S. Appl. No. 15/183,391, Office Action Summary, dated Mar. 26, 2018.
U.S. Appl. No. 15/183,431, Office Action Summary, dated Apr. 12, 2018.
U.S. Appl. No. 15/183,456, Office Action Summary, dated Jan. 26, 2018.
L. Lykouras et al., "Anxiety Disorders and Obesity", Psychiatriki, Oct.-Dec. 2011; 22(4):307-13, (abstract) p. 1.
Barile et al.,"Human milk and related oligosaccharides as prebiotics", Current Opinion in Biotechnology, 2013, pp. 1-6, sciencedirect. com.
Druart et al., "Modulation of the Gut Microbiota by Nutrients with Prebiotic and Probiotic Properties", Proceedings of the IUNS 20th International Congress of Nutrition (Part 2), 2014, pp. 1-10, American Society for Nutrition.
U.S. Appl. No. 15/183,391, Office Action Summary, dated Jun. 14, 2019, pp. 1-35.
David A. Fields et al., "A Narrative Review of the Associations Between Six Bioactive Components in Breast Milk and Infant Adiposity", Obesity, vol. 24 | No. 6 | Jun. 2016, pp. 1213-1221.
Stanley IP et al., "Breastfeeding and Maternal and Infant Health Outcomes in Developed Countries", AHRQ Publication No. 07-E007, Apr. 2007, pp. 1-415.
G. Gibson et al., "The International Scientific Association for Probiotics and Prebiotics (ISAPP) consensus statement pri the definition and scope of prebiotics", Nature Reviews | Gastroenterology & Hepatology, vol. 14, Aug. 2017, pp. 491-502.
USPTO, "Office Action Summary", U.S. Appl. No. 15/104,794 dated Dec. 20, 2018, pp. 1-23.
R. Rosmond et al., "The hypothalamic-pituitary-adrenal axis activity as a predictor or cardiovascular disease, type diabetes and stroke" Journal of Internal Medicine 2000, 247; pp. 188-1979 (Year 2000).
R. Silvennoinen et al., "Acute Psychological Stress Accelerates Reverse Cholesterol Transport Via Corticosteroid-Inhibition of Intestinal Cholesterol Absorption", Circulation Stress 2012, 111(11) pp. 1459-1469 (Year 2012).
L. Deveza et al. "Therapeutic Angiogenesis for Treating Cardiovascular Diseases", Theranostics 2012 2(8), pp. 301-814 (Year 2012).
JSPTO, "Summary of Office Action" U.S. Appl. No. 15/183,431, pp. 1-30, dated Feb. 7, 2019.
U.S. Appl. No. 15/183,431, Office Action Summary, dated Oct. 31, 2019, pp. 1-26.
Olivia Ballard et al., "Human Milk Composition: Nutrients and Bioactive Factors", National Institutes of Health, Pediatr Clin North Am, Feb. 1, 2014, pp. 1-24.
Undurti N. Das, "Breastfeeding prevents type 2 diabetes mellitus: but, how and why?", known about and downloaded from https://academic.oup.com/ajcn/article-abstract/85/5/1436/4633161 on Nov. 12, 2019, pp. 1-2.
David A. Sela et al., "Nursing our microbiota: molecular linkages between bifidobacteria and milk oligosaccharides", National Institutes of Health, Trends Microbiol, Jul. 1, 2011, pp. 1-18.
U.S. Appl. No. 15/104,794, Office Action Summary, dated Aug. 22, 2019, pp. 1-60.
U.S. Appl. No. 15/183,404, Office Action Summary, dated Mar. 20, 2020, pp. 1-52.
J. Chen et al., "Bifidobacterium adolescentis supplementation ameliorates visceral fat accumulation and insulin sensitivity in an experimental model of the metabolic syndrome", British Journal of Nutrition Sep. 14, 2011, 107, 1429-1434.
M. Joossens et al., "Dysbiosis of the faecal microbiota in patients with Crohn's disease and their unaffected relatives", Downloaded from gut.bmj.com on Aug. 22, 2011, pp. 631-637.
D. Guyonne et al. "Effect of a fermented milk containing Bifidobacterium animalis DN-173 010 on the health-related quality of life and symptoms in irritable bowel syndrome in adults in primary care: a multicentre, randomized, double-blind, controlled trial", Alimentary Pharmacology & Therapeutics. Apr. 26, 2007, pp. 475-486.
P.J. Whorewll et al, "Efficcy of an Encasulated Probiotic Bifidobacterium infantis 35624 in Woman with Irritable Bowel Syndrome", American Journal of Gastroenterology, 2006, pp. 1581-1590.
S. Duranti et al., "Genomic Characterization and Transcriptional Studies of the Starch-Utilizing Strain Bifidobacterium adolescentis 22L", Applied and Environmental Microbiology, vol. 80 No. 19, Oct. 2014, pp. 3080-6090.
A.M. Zivkovic, "Human milk glycobiome and its impact on the infant gastrointestinal microbiota", PNAS | Mar. 15, 2011 | vol. 108 | suppl. 1 | pp. 4653-4658.
J.S. Frick et al., "Identification of Commensal Bacterial Strains That Modulate Yersinia enterocolitica and Dextran-Sodium Sulfate-Induced Inflammatory Responses: Implications for the Development of Probiotics", Infection and Immunity, American Society for Microbiology, vol. 75, No. 7, Jul. 2007, pp. 3490-3497.
T. Pozo-Rubio et al., "Immunostimulatory effect of faecal Bifidobacterium species of breast-fed and formula-fed infants in a peripheral blood mononuclear cell/Caco-2 co-culture system", British Journal of Nutrition, 106, May 31, 2011, p. 1216-1223.
R. Martin et al., "Isolation of Bifidobacteria from Breast Milk and Assessment of the Bifidobacterial Population by PCR-Denaturng Gradient Gel Electrophoresis and Quantitative Real-Time PCR", Applied and Environmental Microbiology, vol. 75, No. 4, Feb. 2009, pp. 965-969.
G.V. Coppa et al., "Oligosaccharides in 4 Different Milk Groups, Bifidobacteria, and Ruminococcus obeum", JPGN, vol. 53, No. 1, Jul. 2011, pp. 80-87.
A. Wittmann et al., "Plasmacytoid Dendritic Cells Are Crucial in Bifidobacterium adolescentis-Mediated Inhibition of Yersinia enterocolitica Infection", PLOS, vol. 8, No. 8, Aug. 2013, pp. 1-10.
P. Wacklin et al., "Secretor Genotype (FUT2 gene) Is Strongly Associated with the Composition of Bifidobacteria in the Human Intestine", PLOS, vol. 6 No. 5, May 2011, pp. 1-10.
C. Hoarau et al., "Supernatant of Bifidobacterium breve induces dendritic cell maturation, activation, and survival through a Toll-like receptor 2 pathway", J Allergy Clin Immunol, vol. 117, No. 3, Mar. 2006, pp. 696-702.
L. Chen, "Therapeutic effects of four strains of probiotics on experimental colitis in mice", World J Gastroenterol Jan. 21, 2009; 15(3): pp. 321-327.
U.S. App. No. 15/104,794, Office Action Summary, dated Mar. 6, 2020, pp. 1-52.
U.S. App. No. 15/183,391, Office Action Summary, dated Feb. 19, 2020, pp. 1-30.

(56) References Cited

OTHER PUBLICATIONS

E. Elison et al., "Oral supplementation of healthy adults with 2!-O-fucosyllactose and lacto-N-neotetraose is well tolerated and shills the intestinal microbiota", British Journal of Nutrition, Aug. 22, 2016, pp. 1-13.

G. Gibson et al., "The International Scientific Association for Probiotics and Prebiotics (ISAPP) consensus statement pn the definition and scope of prebiotics", Nature Reviews | Gastroenterology & Hepatology, vol. 14, Aug. 2017, pp. 491-502.

\* cited by examiner

SYNTHETIC COMPOSITION FOR TREATING METABOLIC DISORDERS

CROSS REFERENCE TO RELATED APPLICATIONS

This is a continuation-in-part of U.S. patent application Ser. No. 15/104,794, filed Jun. 15, 2016, which is a national stage filing in accordance with 35 U.S.C. § 371 of PCT/DK2015/050385, filed Dec. 8, 2015, which claims the benefit of the priority of Denmark Patent Application No. PA 2014 70768, filed Dec. 8, 2014, the contents of each are incorporated herein by reference.

SEQUENCE LISTING

The instant application contains a Sequence Listing which has been submitted electronically in ASCII format and is hereby incorporated by reference in its entirety. Said ASCII copy, created on Aug. 30, 2016, is named 4564U_000086_SL.txt and is 1,343 bytes in size.

FIELD OF INVENTION

This invention relates to compositions and methods for stabilising or reducing insulin resistance in patients having an obesity-related, metabolic disorder.

BACKGROUND TO THE INVENTION

Many obese patients have metabolic dysfunctions, even at early stages. These patients tend to develop comorbidities such as type 2 diabetes. Tissue resistance to insulin's actions (insulin resistance) has been postulated as the initial impairment underlying the onset of the metabolic comorbidities in these patients. Consequently, it is a risk factor for development of comorbidities to obesity; especially type 2 diabetes.

Type 2 diabetes is a metabolic disorder that is characterised by hyperglycaemia due to insulin resistance and relative lack of insulin and is a rapidly growing global epidemic. The International Diabetes Federation (IDF) reports that as of 2013 there were more than 382 million people living with diabetes, and a further 316 million with impaired glucose tolerance who are at high risk from the disease (IDF Diabetes Atlas, 6$^{th}$ edn.). The World Health Organization (WHO) furthermore estimates that 90 percent of people around the world who suffer from diabetes suffer from type 2 diabetes. Long-term complications from high blood sugar can include heart disease, strokes, diabetic retinopathy, kidney failure, and poor blood flow in the limbs.

Since it is unlikely that there has been a dramatic alteration in genetic factors in the past decades, environmental factors such as diet must play a key role in the rapid rise in diabetes. Further the gut microbiota has been proposed as a key factor (Burcelin et al. *Frontiers in Bioscience* 14,5107 (2009)) with populations showing marked differences between healthy, obese, and type 2 diabetic patients (Qin et al. *Nature* 490, 55 (2012)). The dysbiosis of gut microbiota has the potential to affect host metabolism and energy storage (Ley et al. *Nature* 444, 1022(2006)) and to affect gut permeability and, as a consequence, give rise to metabolic endotoxemia and higher plasma lipopolysaccharide (LPS). In addition, gut peptides such as glucagon-like peptide 1 (GLP1) and GLP2 can play key roles in these processes (Tremaroli et al. *Nature* 489, 242(2012)). For example, GLP2, which is secreted by intestine L cells, is a key regulator of intestinal permeability (Cani et al. Gut58, 1091 (2009)). Therapeutic regimes that target intestinal microbiota and intestinal barrier therefore show a broad prospect in treating diabetes (Kootte et al. *Diabetes, Obesity & Metabolism* 14, 112 (2012)).

Recent insights suggest that an altered composition and diversity of gut microbiota could play an important role in the development of metabolic disorders such as obesity and diabetes. Gut microbiota does not only participate in whole-body metabolism by affecting energy balance (Turnbaugh et al. *Nature* 444, 1027 (2006)) and glucose metabolism (Cani et al. *Diabetes* 57, 1470 (2008)) but is also involved in development of the low-grade inflammation (Cani et al. *Gut* 58, 1091 (2009)) associated with obesity and related metabolic disorders such as diabetes. The association between inflammation and type 2 diabetes was described in the 1950s, when epidemiological studies showed a rise in acute-phase response proteins in serum of type 2 diabetic patients compared with controls (Fearnley et al. *Lancet* 274, 1067 (1959)). Later, a specific link between inflammatory and metabolic responses was made with the discovery that compared with lean tissue, obese adipose tissue secretes inflammatory cytokines and that these inflammatory cytokines themselves can inhibit insulin signalling (Hotamisligil et al. *Science* 271, 665 (1996)). The definitive proof of a connection between inflammatory mediators and insulin resistance in obesity and type 2 diabetes came from genetic studies that interfered with inflammatory mediators and demonstrated beneficial effects of this interference on insulin action (Uysal et al. *Nature* 389, 610 (1997)).

In recent years, gut microbiota derived LPS has been shown to be involved in the onset and progression of inflammation, and in pathological situations, such as obesity and type 2 diabetes, LPS play a major role in the onset of disease (Cani et al. *Diabetes* 57, 1470 (2008)). After only one week of a high-fat diet in mice, commensal intestinal bacteria are translocated from the intestine into adipose tissue and the blood where they can induce inflammation (Amar et al. *EMBO Mol. Med.* 3, 559 (2011)). This metabolic bacteraemia is characterized by an increased co-localization with dendritic cells from the intestinal lamina propria and by an augmented intestinal mucosal adherence of non-pathogenic *Escherichia coli*. The bacterial translocation process from intestine towards tissue with resulting inflammation was reversed by six weeks of treatment with the probiotic strain *Bifidobacterium animalis* subsp. *lactis* 420, suggesting an involvement of the microbiota.

Normally insulin secretion is proportional to blood glucose levels. However, in some individuals, body tissue does not respond properly to insulin. The insulin receptors in body tissue do not function properly and cells inadequately recognise the presence of insulin. As a result, the pancreas needs to secrete more insulin. This phenomenon is called insulin resistance (or impaired insulin sensitivity). Reducing insulin resistance, or at least preventing its increase, is therefore desired, especially in obese people to prevent or slow down disease progression.

EP-A-1332759 discloses that oral doses of 2'-FL, 3'-SL, 6'-SL, LNnT and sialic acid promote insulin secretion in type 2 diabetes-model mice.

EP-A-2143341 discloses that a mixture of GOS, sialylated oligosaccharides and N-acylated oligosaccharides reduces triglyceride concentration in liver in model mice.

EP-A-2332552 discloses that 3'-SL and 6'-SL reduce/prevent fat accumulation in the liver and other organs in high-fat diet mice and rats.

WO2013/057061 discloses a composition for increasing insulin sensitivity and/or reducing insulin resistance. The composition contains long chain polyunsaturated fatty acids, probiotics and a mixture of oligosaccharides containing at least one of lacto-N-neotetraose (LNnT) and lacto-N-tetraose (LNT), at least one N-acetylated oligosaccharide different from LNnT and LNT, at least one sialylated oligosaccharide and at least one neutral oligosaccharide, for use in increasing insulin sensitivity and/or reducing insulin resistance. This composition can also contain 2'-O-fucosyllactose (2'-FL). The composition is particularly adapted for use in infants who were born preterm and/or who experienced IUGR, and in pregnant women suffering from gestational diabetes. It is also stated that the composition can be given to children, adolescents, and adults suffering from insulin resistance and/or type II diabetes. It is stated that the efficacy of the composition can be the result of the synergistic combination of immunity modulator effects triggered by the probiotics and the LC-PUFA through their stimulation with the specific oligosaccharide mixture.

However, there remains a need for effective interventions which are able to stabilise or improve insulin resistance in patients having an obesity-related, metabolic disorder, which are safe, well tolerated and well accepted.

SUMMARY OF THE INVENTION

In one aspect, this invention provides one or more human milk oligosaccharides (HMOs) for stabilising or reducing insulin resistance in a human individual having an obesity-related metabolic disorder, for example obesity, obesity induced pre-diabetes and obesity induced type 2 diabetes.

Preferably the human milk oligosaccharides include one or more fucosylated HMOs, such as 2'-FL, and one or more core HMOs, such as LNT and LNnT. More preferably the composition comprises a mix of 2'-FL and LNnT; for example in a mass ratio of 5:1 to 1:1; more preferably 4:1 to 2:1.

In another aspect, this invention provides a synthetic composition for stabilising or reducing insulin resistance in a human individual having an obesity-related metabolic disorder, for example obesity, obesity induced pre-diabetes and obesity induced type 2 diabetes, characterised in that the synthetic composition contains an effective amount of one or more human milk oligosaccharides (HMOs).

In another aspect, this invention provides a method for stabilising or reducing insulin resistance in a human individual having an obesity-related metabolic disorder, for example obesity, obesity induced pre-diabetes and obesity induced type 2 diabetes, the method comprising enterally administering to the patient an effective amount of one or more human milk oligosaccharides.

The human individual can be an obese paediatric or adult patient, preferably a prepubescent child.

The HMOs may be administered to the patient as a daily dose of about 1 g to about 15 g such as from about 3 g to about 10 g. The patient can be administered a higher amount, preferably 5 g to 10 g per day, of the HMOs for an initial treatment period, followed by a lower amount, preferably 1 g to 5 g per day, for a maintenance period. The initial treatment period can be 1 to 8 weeks. The maintenance period is at least 1 month.

DETAILED DESCRIPTION OF THE INVENTION

It has been surprisingly found that human milk oligosaccharides, advantageously 2'-FL, LNT and LNnT, not only modulate inflammation and microbiota in the GI tract, but also stabilise or reduce insulin resistance. Further, the abundance of members of the *Bifidobacterium adolescentis* phylogenetic group is increased, in particular *B. adolescentis* and/or *B. pseudocatenulatum*. In particular, a combination of 2'-FL and LNnT preferentially increases the abundance of *B. pseudocatenulatum*. This can result in lower chronic inflammation, improved insulin sensitivity and reduced insulin resistance. Obese and pre-diabetic patients can be stabilised and the progression to diabetes slowed, stopped or reversed. Diabetic patients can be stabilised or at least the progression to diabetes with complications slowed.

Terms and Definitions

The term "patient" preferably means a human individual who was diagnosed by a medical or health professional personal as having a disease, e.g. a metabolic disorder, and receiving or registered to receive medical treatment. The patient can be a paediatric or adult patient.

"Paediatric patient" can be a human patient of 3-21 years old. In some embodiments, a "patient" can also be any other mammal.

The terms "human", "non-infant human" and "non-infant" all mean in the present context a human individual of at least 3 years old. A human can be a child, a teenager, an adult or an elderly, preferably, the human is an individual of at least 3 years old that has an excess of body fat, more preferably, an individual whose excess body fat has accumulated to the extent that it may have a negative effect on health, i.e. an overweight or obese human individual.

The term "obese human individual" means that a human individual that has a body mass index (BMI), a measurement obtained by dividing the individual's weight by the square of the individual's height, over 30 kg/m$^2$, with the range 25-30 kg/m$^2$ defined as overweight.

Overweight and obesity for children and teens (human individuals aged 3-19 years old) is defined as the following: overweight is defined as a BMI at or above the 85th percentile and below the 95th percentile for children and teens of the same age and sex. Obesity is defined as a BMI at or above the 95th percentile for children and teens of the same age and sex (see: Rolland-Cachera, *Int. J. Pediatr. Obesity* 6, 325 (2011)).

The term "enteral administration" means any conventional form for delivery of a composition to a human that causes the deposition of the composition in the gastrointestinal tract (including the stomach). Methods of enteral administration include feeding through a naso-gastric tube or jujenum tube, oral, sublingual and rectal.

The term "oral administration" means any conventional form for the delivery of a composition to a human through the mouth. Accordingly, oral administration is a form of enteral administration.

The term "effective amount" preferably means an amount of a composition that provides a human milk oligosaccharide in a sufficient amount to render a desired treatment outcome in a patient. An effective amount can be administered in one or more doses to the patient to achieve the desired treatment outcome. In some embodiments, the term "effective amount may mean an amount of single HMO, or a combination of different HMOs that is capable of increasing the abundance of bifidobacteria in the gastro-intestinal tract of a human individual of the invention, in particular, relative abundance of members of the *Bifidobacterium adolescentis* phylogenetic group in particular *B. adolescentis* and/or *B. pseudocatenulatum*.

The term "relative abundance of bifidobacteria" means the abundance of bifidobacteria relative to other genus in the microbiota of the gastro-intestinal tract.

The term "human milk oligosaccharide" or "HMO" preferably means a complex carbohydrate consisting of a small number, typically 3-10, of monosaccharide units attached to each other by an interglycosidic linkage that can be found in human breast milk and that can be in acidic or neutral form. More than about 200 different HMO structures are known to exist in human breast milk (Urashima et al.: *Milk Oligosaccharides*, Nova Biomedical Books, New York, 2011). HMOs can be core, fucosylated and sialylated oligosaccharides. Core HMOs are non-fucosylated neutral (that is non-charged) HMOs and consist of Glu, Gal and GlcNAc (thus devoid of Fuc and sialic acid). Examples of core HMOs include lacto-N-tetraose (LNT), lacto-N-neotetraose (LNnT), lacto-N-neohexaose (LNnH), lacto-N-hexaose (LNH) and p-lacto-N-neohexaose (pLNnH). Fucosyl HMOs are fucosylated lactoses or fucosylated core HMOs such as 2'-fucosyllactose (2'-FL), lacto-N-fucopentaose I (LNFP-I), lacto-N-difucohexaose I (LNDFH-I), 3-fucosyllactose (3-FL), difucosyllactose (DFL), lacto-N-fucopentaose III (LNDFP-III), fucosyl-para-lacto-N-neohexaose (F-pLNnH), lacto-N-difucohexaose I (LNDFH-I), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-I), fucosyl-lacto-N-hexaose III (FLNH-III) and fucosyl-para-lacto-N-neohexaose (F-pLNnH). Sialyl HMOs are sialylated lactoses or sialylated core HMOs such as 3',6-disialyllacto-N-tetraose (DSLNT), 6'-sialyllactose (6'-SL), 3'-sialyllactose (3'-SL), 6'-sialyllacto-N-neotetraose (LST c), 3'-sialyllacto-N-tetraose (LST a) and 6-sialyl-lacto-N-tetraose (LST b). Examples for sialylated and fucosylated HMOs include disialyl-fucosyl-lacto-N-hexaose II (DSFLNH-II), fucosyl-sialyl-lacto-N-neohexaose I (FSLNnH-I), fucosyl-sialyl-lacto-N-hexaose I (FSLNH-I) and 3-fucosyl-3'-sialyllactose (FSL).

The HMOs can be isolated or enriched by well-known processes from milk(s) secreted by mammals including, but not limited to human, bovine, ovine, porcine, or caprine species. The HMOs can also be produced by well-known processes using microbial fermentation, enzymatic processes, chemical synthesis, or combinations of these technologies. As examples, using chemistry LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, 6'-SL and salts thereof can be made as described in WO 2010/100979, sialylated oligosaccharides can be made as described in WO 2012/113404 and mixtures of human milk oligosaccharides can be made as described in WO 2012/113405. As examples of enzymatic production, sialylated oligosaccharides can be made as described in WO 2012/007588, fucosylated oligosaccharides can be made as described in WO 2012/127410, and advantageously diversified blends of human milk oligosaccharides can be made as described in WO 2012/156897 and WO 2012/156898. With regard to biotechnological methods, WO 01/04341 and WO 2007/101862 describe how to make core human milk oligosaccharides optionally substituted by fucose or sialic acid using genetically modified *E. coli*.

The human milk oligosaccharides can be in the form of one or more core HMOs and one or more fucosylated HMOs. In a preferred embodiment, a core HMO selected from LNnT and LNT, and 2'FL are used.

The term "intestinal permeability" preferably means the permeability of the intestinal mucosa of a patient, permitting the absorption of vital nutrients from the gut lumen while presenting a barrier against the passage of pathogenic substances into the patient's body.

The term "endotoxemia" preferably means the presence of endotoxins, such as gut microbiota-derived lipopolysaccharides (LPS) in the blood of a patient.

The term "low-grade inflammation" preferably means an immune system response of a patient characterized by altered levels of pro-inflammatory and anti-inflammatory cytokines as well as numerous other markers of immune system activity in response to an injurious stimuli.

The term "relative abundance of bifidobacteria" means the abundance of bifidobacteria relative to other genus in the microbiota of the gastro-intestinal tract.

"Microbiota", "microflora" and "microbiome" preferably mean a community of living microorganisms that typically inhabits a bodily organ or part, particularly the gastro-intestinal organs of non-infant humans. The most dominant members of the gastrointestinal microbiota include microorganisms of the phyla of *Firmicutes, Bacteroidetes, Actinobacteria, Proteobacteria, Synergistetes, Verrucomicrobia, Fusobacteria,* and *Euryarchaeota*; at genus level *Bacteroides, Faecalibacterium, Bifidobacterium, Roseburia, Alistipes, Collinsella, Blautia, Coprococcus, Ruminococcus, Eubacterium* and *Dorea*; at species level *Bacteroides uniformis, Alistipes putredinis, Parabacteroides merdae, Ruminococcus bromii, Dorea longicatena, Bacteroides caccae, Bacteroides thetaiotaomicron, Eubacterium hallii, Ruminococcus torques, Faecalibacterium prausnitzii, Ruminococcus lactaris, Collinsella aerofaciens, Dorea formicigenerans, Bacteroides vulgatus* and *Roseburia intestinalis*. The gastrointestinal microbiota includes the mucosa-associated microbiota, which is located in or attached to the mucus layer covering the epithelium of the gastrointestinal tract, and luminal-associated microbiota, which is found in the lumen of the gastrointestinal tract.

The term "bifidobacteria" means a member of the *Bifidobacterium* genus commonly found in the human gastro-intestinal tract. Examples of bifidobacteria are *Bifidobacterium longum, Bifidobacterium bifidum,* and the members of the phylogenetic *Bifidobacterium adolescentis* group. In non-infant humans, bifidobacteria preferably include members of the phylogenetic *Bifidobacterium adolescentis* group.

The term "*Bifidobacterium* of the *Bifidobacterium adolescentis* phylogenetic group" means a bacterium selected from a group consisting of *Bifidobacterium adolescentis, Bifidobacterium angulatum, Bifidobacterium catenulatum, Bifidobacterium pseudocatenulatum, Bifidobacterium kashiwanohense, Bifidobacterium dentum* and *Bifidobacterium stercoris* (Duranti et al. *Appl. Environ. Microbiol.* 79, 336 (2013), Bottacini et al. *Microbial Cell Fact.* 13:S4 (2014)).

The term "glycemic index" or "GI" is defined as the incremental area under the two-hour blood glucose response curve (AUC) following a 12-hour fast and ingestion of a food with a certain quantity of available carbohydrate (usually 50 g). The AUC of the test food is divided by the AUC of the standard (glucose, the standard, has a GI of 100) and multiplied by 100. The average GI value is calculated from data collected in 10 human subjects. Both the standard and test food must contain an equal amount of available carbohydrate. The result gives a relative ranking for each tested food. Tables reporting commonly accepted GI values for a variety of foods are available including the international GI database maintained by the University of Sydney, and available on the internet at: www.glycemicindex.com.

The term "synthetic composition" means a composition which is artificially prepared and preferably means a composition containing at least one compound that is produced ex vivo chemically and/or biologically, e.g. by means of chemical reaction, enzymatic reaction or recombinantly. In some embodiments a synthetic composition of the invention may be, but preferably is not, identical with a naturally occurring composition. The synthetic composition of the invention typically comprises one or more compounds, advantageously HMOs, that are capable of preferentially increasing the abundance of bifidobacteria, in particular *Bifidobacterium* of the following species: *Bifidobacterium longum, Bifidobacterium bifidum*, and/or members of the phylogenetic *Bifidobacterium adolescentis* group. In some embodiments, the synthetic composition may comprise one or more compounds or components other than HMOs that may have an effect on bifidobacteria of a human subject microbiota in vivo, e.g. non-digestible oligosaccharides or prebiotics. Also in some embodiments, the synthetic compositions may comprise one or more nutritionally or pharmaceutically active components which do not affect adversely the efficacy of the above mentioned compounds. Some non-limiting embodiments of a synthetic composition of the invention are also described below. The synthetic composition can take any suitable form. For example, the composition can be in the form of a nutritional composition which contains other macronutrients such as proteins, lipids or other carbohydrates. The synthetic composition can also be a pharmaceutical composition.

Embodiments of the Invention

One embodiment of the invention relates to an HMO for use in stabilising or reducing insulin resistance in a human individual having an obesity-related metabolic disorder.

Another embodiment of the invention relates to a synthetic composition comprising an HMO for use instabilising or reducing insulin resistance in a human individual having an obesity-related metabolic disorder.

Still another embodiment of the invention relates to a method for stabilising or reducing insulin resistance in a human individual having an obesity-related metabolic disorder, the method comprising enterally administering to the patient an effective amount of one or more human milk oligosaccharides.

The HMO in any of the above embodiments may be a single HMO or a mixture of any HMOs suitable for the purpose of the invention. Preferably, the HMO is a fucosylated or a non-fucosylated neutral HMO. More preferably, the invention relates to a mixture of HMOs, the mixture comprising at least a first HMO and at least a second HMO, wherein the first HMO is a fucosylated neutral HMO and the second HMO is a non-fucosylated neutral HMO. Particularly, the mixture of HMOs may contain a fucosylated HMO selected from the list consisting of 2'-FL, 3-FL, DFL, LNFP-I, LNFP-II, LNFP-III, LNFP-V, LNDFH-I, LNDFH-II, LNDFH-III, FLNH-I, FLNH-II, FLNnH, FpLNH-I and F-pLNnH II, and a non-fucosylated HMO selected from the list consisting of LNT, LNnT, LNH, LNnH, pLNH and pLNnH. Preferably, the mixture of HMOs contains a fucosylated HMO selected from the list consisting of 2'-FL, 3-FL and DFL, and a non-fucosylated HMO selected from the list consisting of LNT and LNnT; advantageously the mixture comprises 2'-FL and LNnT and/or LNT. In some embodiments, the mixture of HMOs essentially consists of two neutral HMOs, e.g. a fucosylated HMO selected from the list consisting of 2'-FL, 3-FL, DFL, LNFP-I, LNFP-II, LNFP-III, LNFP-V, LNDFH-I, LNDFH-II, LNDFH-III, FLNH-I, FLNH-II, FLNnH, FpLNH-I and F-pLNnH II, and a non-fucosylated HMO selected from the list consisting of LNT, LNnT, LNH, LNnH, pLNH and pLNnH. Preferably, the mixture essentially consists of a fucosylated HMO selected from the list consisting of 2'-FL, 3-FL and DFL, and a non-fucosylated HMO selected from the list consisting of LNT and LNnT; in one preferred embodiment the mixture essentially consists of 2'-FL and LNnT, in another preferred embodiment the mixture essentially consists of 2'-FL and LNT.

The invention relates in different embodiments to single HMOs as substantially pure single compounds, i.e. an HMO which grade of purity satisfies the demand of a medical or food authority for marketing, or mixtures of substantially pure HMOs, or artificial compositions comprising one or more HMOs.

Nutritional Compositions

A nutritional composition can contain sources of protein, lipids and/or digestible carbohydrates and can be in solid, powdered or liquid forms. The composition can be designed to be the sole source of nutrition or a nutritional supplement.

Suitable protein sources include intact, hydrolysed, and partially hydrolysed protein, which can be derived from any suitable source such as milk (e.g., casein, whey), animal (e.g., meat, fish), cereal (e.g., rice, corn), and vegetable (e.g., soy, potato, pea), insect (e.g., locust) and combinations of these sources. Examples of the source of protein include whey protein concentrates, whey protein isolates, whey protein hydrolysates, acid caseins, sodium caseinates, calcium caseinates, potassium caseinates, casein hydrolysates, milk protein concentrates, milk protein isolates, milk protein hydrolysates, non-fat dry milk, condensed skim milk, soy protein concentrates, soy protein isolates, soy protein hydrolysates, pea protein concentrates, pea protein isolates, pea protein hydrolysates, collagen proteins, and combinations of these sources.

The amount of protein is preferably sufficient to provide about 5 to about 30% of the energy of the nutritional composition; for example about 10% to about 25% of the energy. Within these ranges, the amount of protein can vary depending upon the nutritional needs of the intended individual.

The nutritional compositions can also include free amino acids such as tryptophan, glutamine, tyrosine, methionine, cysteine, taurine, arginine, carnitine, threonine, serine and proline and combinations of these amino acids. Threonine, serine and proline are important amino acids for the production of mucin which aids gut barrier function.

Any suitable source of other carbohydrates can be used. Examples include maltodextrin, hydrolysed or modified starch or corn starch, glucose polymers, corn syrup, corn syrup solids, rice-derived carbohydrates, sucrose, glucose, fructose, lactose, high fructose corn syrup, honey, sugar alcohols (e.g., maltitol, erythritol, sorbitol, etc.), isomaltulose, sucromalt, pullulan, potato starch, slowly-digested carbohydrates, dietary fibres such as oat fibre, soy fibre, gum arabic, sodium carboxymethylcellulose, methylcellulose, guar gum, gellan gum, locust bean gum, konjac flour, hydroxypropyl methylcellulose, tragacanth gum, karaya gum, gum acacia, chitosan, arabinogalactans, glucomannan, xanthan gum, alginate, pectin, low and high methoxy pectin, cereal beta-glucans (i.e., oat beta-glucan, barley beta-glucan), carrageenan and psyllium, Fibersol™, other resistant starches, and combinations of these carbohydrate.

Preferably the carbohydrate source includes low glycemic index carbohydrates having a GI score of 55 or below. Examples of low glycemic index carbohydrates include sucromalt, Fibersol™ (inulin), maltodextrins having a dextrose equivalence (DE) of less than 15, rice syrup having a dextrose equivalence of less than 15, fructooligosaccharides, resistant starches, starches, fruit sourced fibres, vegetable sourced fibres, beta-glucans, whole grains, soy fibres, oat fibres, locust bean gum, konjac flour, hydroxypropyl methylcellulose, gum acacia, chitosan, arabinogalactans, xanthan gum, alginate, low and high methoxy pectin, carrageenan, psyllium, isomaltulose, glycerine and sugar alcohols.

The nutritional compositions can include carbohydrates in an amount sufficient to provide about 30 to about 70% of the energy of the composition, for example about 35 to about 65% of the energy. Within these parameters, the amount of carbohydrate can vary widely.

Suitable lipid sources include coconut oil, fractionated coconut oil, soy oil, corn oil, olive oil, safflower oil, high oleic safflower oil, medium chain triglycerides, sunflower oil, high oleic sunflower oil, palm and palm kernel oils, palm olein, canola oil, marine oils, cottonseed oils and combinations of these oils. Fractionated coconut oils are a suitable source of medium chain triglycerides. The lipids can contain polyunsaturated fatty acids such as n-3 LC-PUFA. The n-3 LC-PUFA can be a C20 or a C22 n-3 fatty acid. Preferably the n-3 LC-PUFA is docosahexanoic acid (DHA, C22:6, n-3). The source of LC-PUFA can be, for example, egg lipids, fungal oil, low EPA fish oil or algal oil.

The nutritional compositions can include lipids in an amount sufficient to provide about 10 to about 50% of energy of the nutritional composition, for example about 15 to about 40% of the energy.

The nutritional composition preferably also includes vitamins and minerals. If the nutritional composition is intended to be a sole source of nutrition, it preferably includes a complete vitamin and mineral profile. Examples of vitamins include vitamins A, B-complex (such as B1, B2, B6 and B12), C, D, E and K, niacin and acid vitamins such as pantothenic acid, folic acid and biotin. Examples of minerals include calcium, iron, zinc, magnesium, iodine, copper, phosphorus, manganese, potassium, chromium, molybdenum, selenium, nickel, tin, silicon, vanadium and boron.

The nutritional composition can also include a carotenoid such as lutein, lycopene, zeaxanthin, and beta-carotene. The total amount of carotenoid included can vary from about 0.001 µg/ml to about 10 µg/ml. Lutein can be included in an amount of from about 0.001 µg/ml to about 10 µg/ml, preferably from about 0.044 µg/ml to about 5 µg/ml of lutein. Lycopene can be included in an amount from about 0.001 µg/ml to about 10 µg/ml, preferably about 0.0185 µg/ml to about 5 µg/ml of lycopene. Beta-carotene can comprise from about 0.001 µg/ml to about 10 µg/ml, for example about 0.034 µl/ml to about 5 µg/ml of beta-carotene. The nutritional composition can also include a source of anthocyanins. This can be in the form of a fruit or a fruit extract. Particularly useful fruits and fruit extracts include plum/prune, apple, pear, strawberry, blueberry, raspberry, cherry, and their combinations.

The nutritional composition can also contain various other conventional ingredients such as preservatives, emulsifying agents, thickening agents, buffers, fibres and prebiotics (e.g. fructooligosaccharides, galactooligosaccharides), probiotics (e.g. *B. animalis* subsp. *lactis* BB-12, *B. lactis* HN019, *B. lactis* Bi07, *B. infantis* ATCC 15697, *L. rhamnosus* GG, *L. rhamnosus* HNOOI, *L. acidophilus* LA-5, *L. acidophilus* NCFM, *L. fermentum* CECT5716, *B. longum* BB536, *B. longum* AH1205, *B. longum* AH1206, *B. breve* M-16V, *L. reuteri* ATCC 55730, *L. reuteri* ATCC PTA-6485, *L. reuteri* DSM 17938), antioxidant/anti-inflammatory compounds including tocopherols, caroteinoids, ascorbate/vitamin C, ascorbyl palmitate, polyphenols, glutathione, and superoxide dismutase (melon), other bioactive factors (e.g. growth hormones, cytokines, TFG-β), colorants, flavours, and stabilisers, lubricants, and so forth.

The nutritional composition can be in the form of a food, soluble powder, a liquid concentrate, or a ready-to-use formulation. The composition can be eaten, drunk or can be fed via a nasogastric. Various flavours, fibres and other additives can also be present.

The nutritional compositions can be prepared by any commonly used manufacturing techniques for preparing nutritional compositions in solid or liquid form. For example, the composition can be prepared by combining various feed solutions. A protein-in-fat feed solution can be prepared by heating and mixing the lipid source and then adding an emulsifier (e.g. lecithin), fat soluble vitamins, and at least a portion of the protein source while heating and stirring. A carbohydrate feed solution is then prepared by adding minerals, trace and ultra trace minerals, thickening or suspending agents to water while heating and stirring. The resulting solution is held for 10 minutes with continued heat and agitation before adding carbohydrates (e.g. the HMOs and digestible carbohydrate sources). The resulting feed solutions are then blended together while heating and agitating and the pH adjusted to 6.6-7.0, after which the composition is subjected to high-temperature short-time processing during which the composition is heat treated, emulsified and homogenized, and then allowed to cool. Water soluble vitamins and ascorbic acid are added, the pH is adjusted to the desired range if necessary, flavours are added, and water is added to achieve the desired total solid level.

For a liquid product, the resulting solution can then be aseptically packed to form an aseptically packaged nutritional composition. In this form, the nutritional composition can be in ready-to-feed or concentrated liquid form. Alternatively, the composition can be spray-dried and processed and packaged as a reconstitutable powder.

The nutritional composition can also be in the form of a food such as a nutritional bar, a yoghurt, etc. These forms can be produced using standard technologies and processes.

When the nutritional product is a ready-to-feed nutritional liquid, the total concentration of HMSs/HMOs in the liquid, by weight of the liquid, is from about 0.0001% to about 2.0%, including from about 0.001% to about 1.5%, including from about 0.01% to about 1.0%. When the nutritional product is a concentrated nutritional liquid, the total concentration of HMSs/HMOs in the liquid, by weight of the liquid, is from about 0.0002% to about 4.0%, including from about 0.002% to about 3.0%, including from about 0.02% to about 2.0%.

The nutritional composition as any of above described according to the invention contain an effective amount of one or more HMOs, e.g. 2'-FL, LNnT or a mixture of 2'-FL and LnNT, etc.

In one embodiment, a nutritional composition comprises a mixture of 2'-FL and LNnT, wherein the ration of the HMOs is 5:1 to 1:1, e.g. the mass ration of 2'-FL to LnNT is the range from 5:1 to 1:1.

Unit Dosage Forms

The synthetic composition of this invention can also be in a unit dosage form such as a capsule, tablet or sachet. For example, the composition can be in a tablet form comprising the human milk monosaccharides and/or oligosaccharides, and one or more additional components to aid formulation and administration, such as diluents, excipients, antioxidants, lubricants, colorants, binders, disintegrants, and the like.

Suitable diluents, excipients, lubricants, colorants, binders, and disintegrants include polyethylene, polyvinyl chloride, ethyl cellulose, acrylate polymers and their copolymers, hydroxyethyl-cellulose, hydroxypropylmethylcellulose (HPMC), sodium carboxymethylcellulose, polyhydroxyethyl methacrylate (PHEMA), polyvinyl alcohol (PVA), polyvinyl pyrrolidone (PVP), polyethylene oxide (PEO), or polyacrylamide (PA), carrageenan, sodium alginate, polycarbophil, polyacrylic acid, tragacanth, methyl cellulose, pectin, natural gums, xanthan gum, guar gum, karaya gum, hypromellose, magnesium stearate, microcrystalline cellulose, and colloidal silicon dioxide. Suitable antioxidants are vitamin A, carotenoids, vitamin C, vitamin E, selenium, flavonoids, polyphenols, lycopene, lutein, lignan, coenzyme Q10 ("CoQIO") and glutathione.

The unit dosage forms, especially those in sachet form, can also include various nutrients including macronutrients.

Administration Dosing

For stabilising or reducing insulin resistance in a patient having an obesity-related, metabolic disorder, the amount of human milk oligosaccharide(s) required to be administered to the person will vary depending upon factors such as the risk and condition severity, the age of the person, the form of the composition, and other medications being administered to the person. However, the required amount can be readily set by a medical practitioner and would generally be in the range from about 200 mg to about 20 g per day, in certain embodiments from about 1 g to about 15 g per day, from about 3 g to about 10 g per day, in certain embodiments from about 3 g to about 7.5 g per day. An appropriate dose can be determined based on several factors, including, for example, body weight and/or condition, the severity of the condition, being treated or prevented, other ailments and/or diseases, the incidence and/or severity of side effects and the manner of administration. Appropriate dose ranges may be determined by methods known to those skilled in the art.

During an initial treatment phase, the dosing can be higher or lower depending upon the need to boost bifidobacteria abundance or initial tolerance to HMOs. During a maintenance phase, the dosing can be set for chronic long term use. For example, during the initial treatment phase, the dosing can be 500 mg to 20 g per day, preferably 1 g to 15 g per day, more preferably 3 g to 10 g per day. During the maintenance phase, the dosing can be reduced to 200 mg to 10 g per day, preferably 500 mg to 7.5 g per day, more preferably 1 g to 5 g per day.

A synthetic composition of this invention can be co-administered to a patient who is also receiving a standard-of-care medication for obesity or diabetes.

HMO/HMOs or synthetic composition(s) comprising said HMO/HMOs disclosed herein is(are) preferably administered to a patient in need enterally, e.g. orally.

EXAMPLES

Examples are now described to further illustrate the invention:

Example 1

Treating High Fat Diet Induced Obesity and Diabetes 10-week-old C57BL/6J mice (100 mice) are housed in groups of five mice per cage, with free access to food and water. The mice are divided into 10 groups of 10 mice, one control group and 9 treatment groups. All of the mice are fed a high-fat (HF) diet (60% fat and 20% carbohydrates [kcal/100 g], or an HF diet supplemented with HMO (20 g/kg of diet) for 8 weeks. Food and water intake are recorded twice a week. The 9 treatment groups are each administered one of the following: a) 2'-FL, b) 3-FL, c) 3'-SL, d) 6'-SL, e) LNT, f) LNnT, g) LNFP-I, h) DSLNT and i) a combination of these saccharides. The control group is administered the HF diet only. Fresh food is given daily.

Intraperitoneal or oral glucose tolerance tests are performed as follows: 6-h-fasted mice are injected with glucose into the peritoneal cavity (1 g/kg glucose, 20% glucose solution) or by gavage (3 g/kg glucose, 66% glucose solution). Blood glucose is determined with a glucose meter (Roche Diagnostics) on 3.5 µl blood collected from the tip of the tail vein. A total of 20 µl blood is sampled 30 min before and 15 or 30 min after the glucose load to assess plasma insulin concentration.

To assess intestinal permeability in vivo, the intestinal permeability of 4000 Da fluorescent dextran-FITC (DX-4000-FITC) is measured. Mice are fasted for 6 h before given DX-44-FITC by gavage (500 mg/kg body weight, 125 mg/ml). After 1 h and 4 h, 120 ml of blood is collected from the tip of the tail vein. The blood is centrifuged at 4° C., 12 000 g for 3 min. Plasma is diluted in an equal volume of PBS (pH 7.4) and analysed for DX-4000-FITC concentration with a fluorescence spectrophotometer at an excitation wavelength of 485 nm and emission wavelength of 535 nm. Standard curves are obtained by diluting FITC-dextran in non-treated plasma diluted with PBS (1:3 v/v).

Plasma LPS, cytokines and gut hormones are determined as follows. Plasma LPS concentration is measured using a kit based upon a Limulus amoebocyte extract (LAL kit endpoint- QCL1000). Samples are diluted 1/40 to 1/100 and heated for 20 cycles of 10 min at 68° C. and 10 min at 4° C. An internal control for LPS recovery is included in the calculation. Plasma cytokines (interleukin (IL) 1α, IL1b, tumour necrosis factor (TNF) α, IL6, monocyte chemoattractant protein (MCP)-1, macrophage inflammatory protein (MIP)-1α, IL10, interferon (INF) c, IL15, IL18) and gut hormones (GLP-1 (active), GIP (total), amylin (active), pancreatic polypeptide) are respectively determined in duplicate by using a Bio-Plex Multiplex kit, or a mouse gut hormones panel (LincoPlex), and measured by using Luminex technology, an EIA kit (GLP-2 EIA kit) is used to quantify GLP-2.

Mice are anaesthetised (ketamine/xylazine, intraperineally, 100 and 10 mg/kg, respectively) after a 5 h period of fasting, and blood samples and tissues are harvested for further analysis. Mice are killed by cervical dislocation. Liver, caecum (full and empty), muscles (vastus lateralis), and adipose tissues (mesenteric and corresponding lymph nodes, epididymal, subcutaneous and visceral) are precisely dissected and weighed. The intestinal segments (jejunum, colon) are immersed in liquid nitrogen, and stored at −80° C., for further analysis.

To assess the microbiota profile, the caecal contents collected post mortem from mice are stored at −80° C. DNA is isolated from the caecal content samples using QIAamp DNA Stool Mini Kit. The DNA concentration of extracts is measured using NanoDrop. Aliquots of 100 ng of extracted DNA are subjected to PCR using the 16S rDNA universal heteroduplex analysis (HDA) primers HDA1-GC 50-CG-CCCGGGGCGCGCCCCGGGCGGG-GCGGGGGC ACG-GGGGGACTCCTACGGGAGGCAGCAGT-30 (SEQ ID NO: 1) and HDA2 50-TTACCGCGGCTGCTGGCA-30

(SEQ ID NO: 2)(both primers are disclosed in Walter et al. *Appl. Environ. Microbiol.* 66, 297 (2000)) at 56° C. for strand annealing. Initial denaturation at 94° C. for 4 min is followed by thirty cycles of 30 s at 94° C., 30 s at 56° C. and 1 min at 72° C. The quality of PCR products is verified by agarose gel electrophoresis. Amplified 16S rDNA fragments are separated by denaturing gradient gel electrophoresis (DGGE) using an INGENYphorU system equipped with 6% polyacrylamide gels with a denaturant in the range of 30-55%, where 100% denaturant is equivalent to 7M-urea and 40% formamide. Electrophoresis is carried out at 130V for 4-5 hours at 60° C. Polyacrylamide gels are stained with GelRede nucleic acid stain for 45 min, destained in ultrapure water and viewed under UV light. Bands of interest are excised from gels and lysed in ultrapure water. Extracted DNA is re-amplified using the same primers and PCR conditions. To purify the bacterial DNA, PCR products are reloaded on a denaturant gradient gel followed by excision and lysis of selected bands. DNA samples recovered from lysed bands of the second DGGE are re-amplified by PCR before purification using the QIAquick PCR Purification Kit and sequenced. Species identification is done using the Ribosomal Microbiome Database Project Classifier tool. Because of the limited sensitivity of DGGE to quantify microbial diversity, the microbial composition of DNA samples is also analysed using high-throughput sequencing. The V5-V6 region of 16S rRNA from caecal content DNA samples is amplified using the primers 784F 50-AGGATTA-GATACCCT-GGTA-30(SEQ ID NO: 3) and 1061R 50-CRRCACGAGCTGACGAC-30(SEQ ID NO: 4) 3640 (both primers are disclosed in Andersson et al. *PloS ONE*3, e2836 (2008)). Amplicons are pyrosequenced using a Roche 454 GS-FLX system. Sequences of at least 240 nucleotides and containing no more than two undetermined bases are retained for taxonomic assignment. The QIIME software is used for chimera check and the Greengenes database is used for classification. Bacterial diversity is determined at the phylum, family and genus levels.

To assess bacterial translocation from intestine into tissues, mesenteric adipose tissue (MAT) and corresponding lymph nodes (MLN) are harvested, and luminal and mucosal contents of each intestinal segment separated. Quantification of bacterial DNA is performed by isolating genomic DNA from blood, MAT, MLN or intestine (contents and mucosa). All bacterial DNA is quantified by quantitative real-time PCR targeting conserved regions of the 16S rRNA gene, with bacterial DNA as standard template for absolute quantification.

In order to assess barrier permeability, the expression of occludin and zonula occludens-1 (ZO-1) tight-junction proteins are assessed. Jejunum segments are immediately removed, washed with PBS, mounted in embedding medium, and stored at −80° C. until use. Cryosections (5 mm) are fixed in acetone at −20° C. for 5 min for occludin and in ethanol for 30 min at room temperature and in acetone at −20° C. for 5 min for ZO-1. Non-specific background is blocked by incubation with 10% bovine serum albumin (BSA) in Tris-buffered saline (TBS) and 0.3% Triton X-100 (30 min at room temperature). Sections are incubated with rabbit anti-occludin or rabbit anti-ZO-1 (1:400 for ZO-1 and 1:100 for occludin staining) for 2 h. Sections are washed three times for 10 min in TBS and probed with goat anti-rabbit fluorescein isothiocyante (FITC)-conjugated antibodies (1:50). Slides are washed three times for 10 min in TBS and mounted in mounting medium. Sections are visualised on a fluorescence microscope. As a control, slides are incubated with serial dilutions of the primary antibody to signal extinction. Two negative controls are used: slides incubated with irrelevant antibody or without primary antibody. All the stainings are performed in duplicate in non-serial distant sections, and analysed in a double-blind manner by two different investigators.

The results show that HMOs improve gut barrier function and reduce the metabolic inflammation and insulin resistance associated with obesity, and increase release of gut peptides, such as glucagon-like peptide-1 and -2 (GLP-1 and -2).

Example 2

Treating Obesity Induced Diabetes

Six-week-old ob/ob mice (120 mice) on C57BL/6 background are housed in a controlled environment (12 h daylight cycle) in groups of 2 mice/cage, and kept with free access to food and drinking water. The mice are separated into 10 groups of 10 mice, one control group and 9 treatment groups. One group is fed a control diet, and the 9 treatment groups each receive a control diets containing one of the following HMOs (20 g/kg of diet) for five weeks: a) 2'-FL, b) 3-FL, c) 3'-SL, d) 6'-SL, e) LNT, f) LNnT, g) LNFP-I, h) DSLNT, and i) a combination of these saccharides. Fresh food is given daily.

Experiments to show impact of HMOs on glucose tolerance, intestinal permeability plasma LPS, cytokines and gut hormones, caecal microbiota profile and bacterial translocation are performed as described under Example 1.

Example 3

Human Trial in Overweight and Obese Children

A total of 60 male and female patients, enrolled to a childhood obesity treatment program, are recruited to participate in the study. Patients are randomized into three groups, each of 20 patients, with 2 groups receiving different investigational products and one group receiving a placebo product for 8 weeks. The investigational products contain 4.5 grams of either 2'-FL alone or a combination of 2'-FL and LNnTin a 4:1 ratio. The placebo product contains 4.5 grams glucose. All products are in powder form in a unit dosage container.

The patients are eligible to participate if: they are between 5 and 10 years of age, have a BMI SDS (Standard Deviation Score) of ≥2.0 and are enrolled in the childhood obesity treatment program at the Children's Obesity Clinic. All recruited patients and their representatives are able and willing to understand and comply with the study procedures. Patients are excluded if: they have participated in a clinical study one month prior to the screening visit and throughout the study; have any gastrointestinal disease(s) that may cause symptoms or may interfere with the trial outcome; have other severe disease(s) such as malignancy, kidney disease or neurological disease; have psychiatric disease; have used highly dosed probiotic supplements (yoghurt allowed) 3 months prior to screening and throughout the study; have consumed antibiotic drugs 3 months prior to screening and throughout the study; and consume on a regular basis medication that might interfere with symptom evaluation 2 weeks prior to screening and throughout the study.

At the initial visit (screening) patients and their representatives are given both oral and written information about the study; the children are asked for informed assent and their representatives to sign an informed consent form.

Eligibility criteria are checked and for children who are enrolled to the study, medical history and concomitant medication are registered. A physical examination is done and pubertal staging is determined. Blood pressure, pulse rate, height and bodyweight are measured, and body composition is determined by a DXA (dual energy x-ray absorptiometry)-scan and bioimpedance. BMI SDS is calculated, waist and hip circumferences measured and food intake registered. Fasting blood samples are collected for safety and biomarker studies and for biobanking.

The serum from the blood samples is transferred to cryotubes and stored at −80° C. The following biomarkers are measured; Lipopolysaccharides (LPS), hsCRP, free fatty acids, total cholesterol, HDL, LDL, HbA1c, glucose, insulin, triglycerides, TNF-α, IL-β, IL-6, IL-8, IL-10, GLP-1, GLP-2, Adiponectin, and Zonulin.

Equipment for collecting faecal samples is distributed. The faecal samples are stored at −80° C. until analysis. Microbiological analysis is performed on the faecal samples using 16S rRNA gene sequencing.

The Rome III Diagnostic Questionnaire for Paediatric Functional GI Disorders (QPFG) is completed on site by the participating child's representative(s), and the Bristol Stool Form Scales (BSFS) is distributed to the participant's representative(s) with instructions to assess the stool consistency at each faecal sampling point using the BSFS.

At the second visit (randomization), patients and their representatives are asked about adverse events, faecal samples are collected and equipment for collection of new samples is distributed. BSFS is collected and new BSFS is distributed. Study products are distributed together with a compliance form (diary). Patients and their representatives are reminded to follow the healthy dietary habits.

The study runs for 8 weeks with the patients consuming either a placebo or one of two investigational products daily. Patients are instructed to consume the products in the morning with breakfast. Compliance is monitored via a compliance form (diary) to be filled in daily.

Four weeks after commencement there is an intermediate check. Patients and their representatives are asked about adverse events and any changes in the patient's usual medication. Faecal samples are collected and equipment for collection of new samples is distributed. Blood pressure, pulse rate, waist and hip circumference, height and bodyweight are measured and BMI SDS calculated. The QPFG questionnaire is completed on site by the participating child's representative. The BSFS is collected and new BSFS is distributed to the participant's representative(s) with instructions to assess the stool consistency at each faecal sampling point using the BSFS. Patients and their representatives are reminded to follow the healthy dietary habits.

At the end of intervention (8 weeks), each patient has a visit with the medical team. Patients and their representatives are asked about adverse events and any changes in the patient's usual medication. Study products and compliance forms are collected to check compliance. BSFS and faecal samples are collected and equipment for collection of new samples is distributed. A physical examination is done and pubertal staging is determined. Blood pressure, pulse rate, height and bodyweight are measured, and body composition is determined by a DXA (dual energy x-ray absorptiometry)-scan and bioimpedance. BMI SDS is calculated, waist and hip circumferences measured and food intake registered. Fasting blood samples are collected for safety and biomarker studies and for biobanking, and equipment for collecting faecal samples is distributed. The QPFG questionnaire is completed on site by the participating child's representative(s).

To examine potential long term effects of the intervention, an un-blinded follow-up period follows with a visit 8 weeks after end of intervention. A physical examination is done and pubertal staging is determined. Blood pressure, pulse rate, height and bodyweight are measured, and body composition is determined by a DXA (dual energy x-ray absorptiometry)-scan and bioimpedance. BMI SDS is calculated, waist and hip circumferences measured and food intake registered. Fasting blood samples are collected for safety and biomarker studies and for biobanking. Faecal samples are collected.

The patients receiving the intervention product have lower HOMA-IR scores. Further the patients given the investigational products show a greater reduction of body fat, body weight and BMI SDS as compared to the placebo group. The blood biomarker analysis indicates that the patients given the investigational products have increased levels of GLP-1 and GLP-2, reduced levels of metabolic endotoxemia and inflammatory markers and reduced gut permeability indicating an improved mucosal barrier compared to the placebo. The faecal analysis indicates that the patients given the investigational products have reduced bacterial dysbiosis and a higher level of bifidobacteria compared to the placebo, particularly *Bifidobacteriumpseudocatenulatum*.

Example 4

Nutritional Composition

A ready to feed nutritional composition is prepared from water, maltodextrin, milk protein concentrate, Sucromalt, glycerine, cocoa powder, soy protein isolate, fructose, high oleic safflower oil, soy oil, canola oil, plant sterol esters, HMOs, soy lecithin, magnesium chloride, calcium phosphate, carrageenan, sodium ascorbate, potassium citrate, sodium phosphate, calcium citrate, choline chloride, potassium chloride, sodium citrate, magnesium oxide, taurine, L-carnitine, alpha-tocopheryl acetate, zinc sulphate, ferrous sulphate, niacinamide, calcium pantothenate, vitamin A palmitate, citric acid, manganese sulphate, pyridoxine hydrochloride, vitamin D3, copper sulphate, thiamine mononitrate, riboflavin, beta carotene, folic acid, biotin, potassium iodide, chromium chloride, sodium selenate, sodium molybdate, phytonadione, vitamin B12.

The composition has an energy density of 0.8 kcal/ml with anenergy distribution (% of kcal) as follows: protein: 20%, carbohydrate: 48%, fat: 32%.

Example 5

Tablet Composition

A tablet is prepared from HMO, hydroxypropyl methylcellulose, sodium alginate, gum, microcrystalline cellulose, colloidal silicon dioxide, and magnesium stearate. All raw materials except the magnesium stearate are placed into a high shear granulator and premixed. Water is sprayed onto the premix while continuing to mix at 300 rpm. The granulate is transferred to a fluidised bed drier and dried at 75° C. The dried powder is sieved and sized using a mill. The resulting powder is then lubricated with magnesium stearate and pressed into tablets. The tablets each contain 325 mg of HMO. The tablets each have a weight of 750 mg.

Example 6

Capsule Composition

A capsule is prepared by filling about 1 g of HMO into a 000 gelatine capsule using a filing machine. The capsules are then closed. The HMO are in free flowing, powder form.

The invention claimed is:

1. A method comprising:
administering to a non-infant patient having an obesity-related metabolic disorder and being diagnosable with one or more of obesity, obesity-induced pre-diabetes, and obesity-induced type 2 diabetes, a product consisting of an effective amount of one or more neutral human milk oligosaccharides (HMOs) comprising at least one fucosylated HMO selected from 2'-fucosyllactose (2'-FL), 3-fucosyllactose (3-FL), and difucosyllactose (DFL), and at least one non-fucosylated HMO selected from lacto-N-tetraose (LNT) and lacto-N-neotetraose (LNnT), wherein the one or more neutral HMOs are administered in an amount effective to:
increase a relative abundance of *Bifidobacterium adolescentis* in the non-infant patient; and
improve in the non-infant patient at least one condition selected from increased insulin sensitivity, reduced insulin resistance, improved gut barrier function, and reduction of metabolic inflammation.

2. The method according to claim 1, wherein the non-infant patient is an obese pediatric patient.

3. The method according to claim 1, wherein the one or more neutral HMOs are synthetic HMOs.

4. The method according to claim 3, wherein the effective amount of the neutral HMOs is administered in a unit dosage form.

5. The method according to claim 1, wherein the mass ratio of 2'-FL present to LNnT present in a selected combination of the one or more neutral HMOs is 5:1 to 1:1.

6. The method of claim 1, wherein the effective amount administered is from about 3 g to about 10 g per day of the one or more neutral HMOs.

7. A method comprising:
administering to a non-infant patient having an obesity-related metabolic disorder an effective amount of one to five neutral human milk oligosaccharides (HMOs) comprising at least one fucosylated HMO selected from 2'-fucosyllactose (2'-FL), 3-fucosyllactose (3-FL), and difucosyllactose (DFL), and at least one non-fucosylated HMO selected from lacto-N-tetraose (LNT) and lacto-N-neotetraose (LNnT) wherein the one to five neutral HMOs are administered in an amount effective to:

increase a relative abundance of *Bifidobacterium adolescentis* in the gastrointestinal microbiota of the non-infant patient; and improve in the non-infant patient at least one condition selected from reduced metabolic endotoxemia, an improved level of a glucagon-like peptide, and reduction in an inflammatory marker associated with the metabolic disorder.

8. The method of claim 7, wherein a mass ratio of 2'-FL present to LNnT present in the effective amount is from 5:1 to 1:1.

9. A method comprising:

administering to a non-infant patient having an obesity-related metabolic disorder a synthetic composition consisting of an effective amount of one or more neutral HMOs selected from 2'-FL, 3'-FL, DFL, LNT, and LNnT, and optionally one or more excipients, wherein the one or more neutral HMOs are administered in an amount effective to:

increase a relative abundance of *Bifidobacterium adolescentis* in the gastrointestinal microbiota of the non-infant patient; and improve in the non-infant patient at least one condition selected from increased insulin sensitivity, reduced insulin resistance, and improved gut barrier function.

10. The method of claim 9, wherein the one or more neutral HMOs consist of 2'-FL, and optionally one of LNT and LNnT.

11. The method of claim 9, wherein the mass ratio of 2'-FL present to LNnT present in a selected combination of the one or more neutral HMOs is 5:1 to 1:1.

12. The method of claim 9, wherein the effective amount of one or more neutral HMOs are effective to increase levels of at least one glucagon-like peptide ("GLP") selected from GLP-1 and GLP-2 when administered to the non-infant patient.

\* \* \* \* \*

SEQUENCE LISTING

```
<160> NUMBER OF SEQ ID NOS: 4

<210> SEQ ID NO 1
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgcccggggc gcgccccggg cggggcgggg gcacgggggg actcctacgg gaggcagcag      60
t                                                                     61

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttaccgcggc tgctggca                                                   18

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aggattagat accctggta                                                  19

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
crrcacgagc tgacgac                                                    17
```